US008877315B2

(12) United States Patent
Yano et al.

(10) Patent No.: US 8,877,315 B2
(45) Date of Patent: Nov. 4, 2014

(54) INDOLIUM COMPOUND AND OPTICAL RECORDING MATERIAL CONTAINING THE SAME

(75) Inventors: Toru Yano, Tokyo (JP); Yohei Aoyama, Tokyo (JP)

(73) Assignee: Adeka Corporation, Tokyo (JP)

( * ) Notice: Subject to any disclaimer, the term of this patent is extended or adjusted under 35 U.S.C. 154(b) by 1002 days.

(21) Appl. No.: 12/674,079

(22) PCT Filed: Sep. 26, 2008

(86) PCT No.: PCT/JP2008/067511
§ 371 (c)(1),
(2), (4) Date: Feb. 18, 2010

(87) PCT Pub. No.: WO2009/050999
PCT Pub. Date: Apr. 23, 2009

(65) Prior Publication Data
US 2011/0111162 A1      May 12, 2011

(30) Foreign Application Priority Data
Oct. 15, 2007    (JP) .................................. 2007-267682

(51) Int. Cl.
G11B 7/24       (2013.01)
C07D 401/06     (2006.01)
C07D 413/14     (2006.01)
G11B 7/247      (2013.01)
C07D 403/06     (2006.01)
C07D 409/14     (2006.01)
C07D 405/06     (2006.01)
C07F 17/02      (2006.01)
C07D 409/06     (2006.01)
G11B 7/246      (2013.01)
C07D 413/06     (2006.01)
C09B 23/10      (2006.01)

(52) U.S. Cl.
CPC ............ *C07D 401/06* (2013.01); *C07D 413/14* (2013.01); *G11B 7/247* (2013.01); *C07D 403/06* (2013.01); *C07D 409/14* (2013.01); *C07D 405/06* (2013.01); *C07F 17/02* (2013.01); *C07D 409/06* (2013.01); *G11B 7/246* (2013.01); *C07D 413/06* (2013.01); *C09B 23/105* (2013.01)
USPC ..................... 428/64.8; 428/64.4; 430/270.18

(58) Field of Classification Search
CPC ... C07D 209/60; C07D 209/62; G11B 7/2472
USPC ............ 428/64.4, 64.8; 430/270.18; 548/427
See application file for complete search history.

(56) References Cited

U.S. PATENT DOCUMENTS

| | | | |
|---|---|---|---|
| 7,683,184 B2 | 3/2010 | Yanagisawa et al. | |
| 2002/0001774 A1 | 1/2002 | Je et al. | |
| 2002/0028918 A1 | 3/2002 | Kasada et al. | |
| 2003/0202458 A1 | 10/2003 | Wang et al. | |
| 2003/0203148 A1 | 10/2003 | Huang et al. | |
| 2005/0031993 A1* | 2/2005 | Yano et al. ............... | 430/270.21 |
| 2007/0255058 A1 | 11/2007 | Yanagisawa et al. | |

FOREIGN PATENT DOCUMENTS

| | | |
|---|---|---|
| CN | 101031544 | 9/2007 |
| EP | 2003172 A1 * | 12/2008 |
| JP | 10219124 A * | 8/1998 |
| JP | 11-034489 | 2/1999 |
| JP | 11-170695 | 6/1999 |
| JP | 2001-342366 | 12/2001 |
| JP | 2002-206061 | 7/2002 |
| JP | 2003-231359 | 8/2003 |
| JP | 2003-313447 | 11/2003 |
| JP | 2003-321450 | 11/2003 |
| JP | 2006-089434 | 4/2006 |
| JP | 2006-150841 | 6/2006 |
| JP | 2007-152829 | 6/2007 |
| WO | WO 2006035554 A1 * | 4/2006 |
| WO | WO 2007/090765 | 8/2007 |
| WO | WO 2007/114074 | 10/2007 |

OTHER PUBLICATIONS

Machine translation of detailed description of JP10-219124 acquired on Feb. 25, 2013.*
Machine translation of detailed description of JP2007-152829 acquired on Feb. 25, 2013.*
Notice of Rejection mailed Jun. 5, 2012 by the Japanese Patent Office in corresponding Japanese Patent Application No. 2007-267682, with English translation.
International Search Report, PCT/JP2008/067511, Nov. 18, 2008.
CN Office Action dated Aug. 2, 2012, with English translation; Application No. 200880102630.2.

* cited by examiner

*Primary Examiner* — Gerard Higgins
(74) *Attorney, Agent, or Firm* — Young & Thompson

(57) ABSTRACT

A novel indolium compound of general formula (I) and an optical recording material containing the indolium compound.

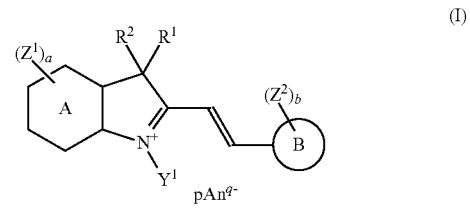

In formula (I), ring A is a benzene ring, etc.; ring B is a 5- or 6-membered heterocyclic ring; $R^1$ is a group of general formula (II), etc.; $R^2$ is an organic group having 1 to 30 carbon atoms, etc.; $Y^1$ is an alkyl group having 1 to 10 carbon atoms, etc.; $Z^1$ and $Z^2$ are each, e.g., an alkyl group having 1 to 8 carbon atoms optionally substituted with a halogen atom and optionally interrupted by —O—, etc.; a is an integer of 0 to 6; b is an integer of 0 to 5; $An^{q-}$ is a q-valent anion; q is 1 or 2; and p is a number necessary to neutralize an electric charge.

1 Claim, No Drawings

INDOLIUM COMPOUND AND OPTICAL RECORDING MATERIAL CONTAINING THE SAME

TECHNICAL FIELD

This invention relates to a novel indolium compound used mainly in an optical recording material and an optical recording material containing the indolium compound. More particularly, it relates to an optical recording material used in an optical recording medium on which information can be written as an information pattern mostly with a laser beam, especially an optical recording medium capable of high-density optical writing and reading using a low energy laser having a wavelength in the visible to ultraviolet region.

BACKGROUND ART

Optical recording media have widely spread generally because of their superiority, such as high recording capacity and non-contact write/read system. Recordable optical disks, such as WORMs, CD-Rs, and DVD±Rs, record information by irradiating a very small area of the optical recording layer thereof with a focused laser beam to change the properties of the irradiated area and reproduce the recorded information making use of the difference in reflected light quantity between the recorded and non-recorded areas.

Compounds having an intense absorption, particularly an absorption maximum ($\lambda_{max}$), in the range of from 550 to 620 nm are used as an optical recording material forming an optical recording layer of an optical recording medium, such as DVD-R.

There are many reports on indolium compounds having an indole ring for use as the optical recording material discussed above in view of their high sensitivity and possibility to respond to the increasing writing speed. For example, patent documents 1 to 6 listed below report styryl indolium compounds. Patent document 7 (see below) reports a low temperature decomposing cyanine compound having an indole ring and a benzyl group introduced into the 3-position of the indole ring. Patent document 8 (see below) discloses an indolium compound having a benzyl group introduced to the 3-position of the indole ring. Low temperature decomposing compounds readily form recorded portions (pits) in an optical recording layer and are considered suited for use in high-speed recording media. However, these materials are unsatisfactory in performance properties including heat resistance, light resistance, and recording characteristics.

Patent document 1: JP 11-34489A
Patent document 2: JP 11-170695A
Patent document 3: JP 2001-342366A
Patent document 4: JP 2002-206061A
Patent document 5: JP 2003-313447A
Patent document 6: JP 2003-321450A
Patent document 7: JP 2003-231359A
Patent document 8: JP 2006-150841A

DISCLOSURE OF THE INVENTION

Problem to be Solved by the Invention

An object of the invention is to provide an indolium compound having high heat and light resistance and exhibiting thermal decomposition behavior suited for use in high-speed optical recording and an optical recording material containing the indolium compound.

Means for Solving the Problem

As a result of extensive investigations, the present inventors have found that an indolium compound having a specific cation structure exhibits good thermal decomposition behavior as an optical recording material and thus reached the present invention.

The above object of the invention is accomplished by the provision of an indolium compound represented by general formula (I):

[Formula 1]

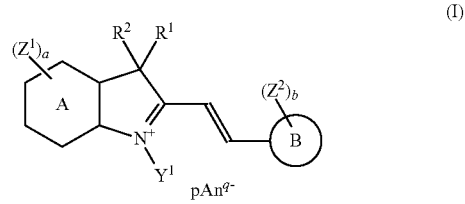

wherein ring A represents a benzene ring or a naphthalene ring; ring B represents a 5- or 6-membered heterocyclic ring; $R^1$ represents a group represented by general formula (II), (II'), or (III); $R^2$ represents an organic group having 1 to 30 carbon atoms or a group represented by general formula (II), (II'), or (III); $Y^1$ represents a hydrogen atom, an alkyl group having 1 to 10 carbon atoms, an aryl group having 6 to 20 carbon atoms, or an arylalkyl group having 7 to 20 carbon atoms; $Z^1$ and $Z^2$ each represent an alkyl group having 1 to 8 carbon atoms optionally substituted with a halogen group and optionally interrupted by —O—, —CO—, —COO—, or —COO—, a sulfonyl group having a hydrocarbon group having 1 to 8 carbon atoms, a sulfinyl group having a hydrocarbon group having 1 to 8 carbon atoms, an alkylamino group having an alkyl group containing 1 to 8 carbon atoms, a dialkylamino group having an alkyl group containing 1 to 8 carbon atoms, a group represented by general formula (III), a cyano group, a nitro group, a hydroxyl group, or a halogen group; a plurality of $Z^2$ substituents may be joined to form a ring structure; a represents an integer of 0 to 6; b represents an integer of 0 to 5; $An^{q-}$ represents a q-valent anion; q represents 1 or 2; and p represents a number necessary to neutralize an electric charge,

[Formula 2]

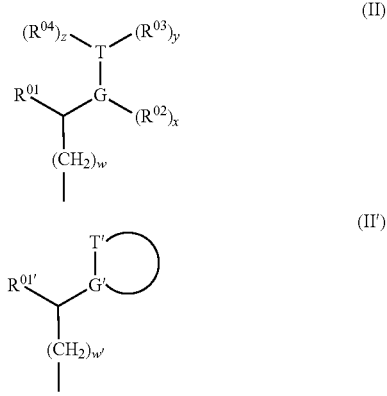

in general formula (II), the bond between G and T is a double bond, a conjugated double bond, or a triple bond; G represents a carbon atom; T represents a carbon atom, an oxygen atom, or a nitrogen atom; x, y, and z each represent 0 or 1, provided that, when T is oxygen, y=z=0, and, when T is nitrogen, y+z=0 or 1; w represents an integer of 0 to 4; $R^{01}$, $R^{02}$, $R^{03}$, and $R^{04}$ each independently represent a hydrogen atom, a hydroxyl group, a nitro group, a cyano group, a halogen atom, an alkyl group having 1 to 4 carbon atoms optionally substituted with a halogen atom, or an alkoxy group having 1 to 4 carbon atoms optionally substituted with a halogen atom; $R^{01}$ and $R^{04}$ may be joined to form a cycloalkene ring or a heterocyclic ring, in general formula (II'), the bond between G' and T' is a double bond or a conjugated double bond; G' represents a carbon atom; T' represents a carbon atom or a nitrogen atom; w' represents an integer of 0 to 4; $R^{01'}$ represents a hydrogen atom, a hydroxyl group, a nitro group, a cyano group, a halogen atom, an alkyl group having 1 to 4 carbon atoms optionally substituted with a halogen atom, or an alkoxy group having 1 to 4 carbon atoms optionally substituted with a halogen atom; the ring containing G' and T' is a 5-membered ring optionally containing a hetero atom, a 6-membered ring optionally containing a hetero atom, a naphthalene ring, a quinoline ring, an isoquinoline ring, an anthracene ring, or an anthraquinone ring; the ring containing G' and T' may be substituted with a halogen atom, a hydroxyl group, a nitro group, a cyano group, an alkyl group having 1 to 4 carbon atoms, or an alkoxy group having 1 to 4 carbon atoms,

[Formula 3]

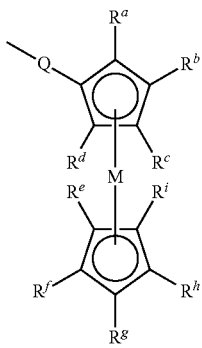

(III)

wherein $R^a$, $R^b$, $R^c$, $R^d$, $R^e$, $R^f$, $R^g$, $R^h$, and $R^i$ each independently represent a hydrogen atom or an alkyl group having 1 to 4 carbon atoms a methylene moiety of which may be interrupted by —O— or —CO—; Q represents a single bond or an optionally substituted alkylene group having 1 to 8 carbon atoms a methylene moiety of which may be displaced by —O—, —S—, —CO—, —COO—, —OCO—, —SO$_2$—, —NH—, —CONH—, —NHCO—, —N=CH—, or —CH=CH—; and M represents Fe, Co, Ni, Ti, Cu, Zn, Zr, Cr, Mo, Os, Mn, Ru, Sn, Pd, Rh, Pt, or Ir.

In a preferred embodiment of the invention, the object of the invention is accomplished by the provision of the indolium compound of general formula (I) which is represented by general formula (IV):

[Formula 4]

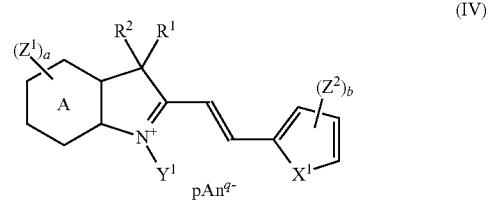

(IV)

wherein ring A, $R^1$, $R^2$, $Z^1$, $Z^2$, $Y^1$, a, b, $An^{q-}$, p, and q are as defined for general formula (I); $X^1$ represents —$NR^5$—, an oxygen atom, a sulfur atom, or a selenium atom; and $R^5$ represents a hydrogen atom, an alkyl group having 1 to 10 carbon atoms, an aryl group having 6 to 20 carbon atoms, or an arylalkyl group having 7 to 20 carbon atoms, the alkyl, the aryl, and the arylalkyl groups being optionally substituted with a halogen group and optionally interrupted by —O—, —CO—, —COO—, or —COO—.

In a still preferred embodiment of the invention, the object of the invention is accomplished by the provision of the indolium compound of general formula (IV) which is represented by general formula (V):

[Formula 5]

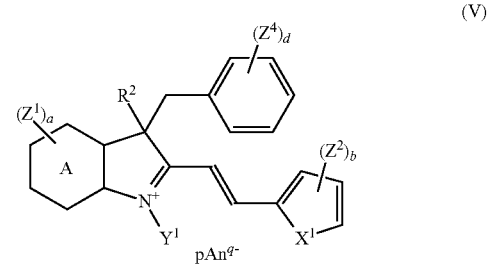

(V)

wherein ring A, $R^2$, $Z^1$, $Z^2$, $Y^1$, a, b, $An^{q-}$, p, and q are as defined for general formula (I); $X^1$ is as defined for general formula (IV); $Z^4$ represents a halogen atom, a hydroxyl group, a nitro group, a cyano group, an optionally halogen-substituted alkyl group having 1 to 4 carbon atoms, or an optionally halogen-substituted alkoxy group having 1 to 4 carbon atoms; and d represents an integer of 0 to 5.

In another still preferred embodiment of the invention, the object of the invention is accomplished by the provision of the indolium compound of general formula (IV) which is represented by general formula (VI):

[Formula 6]

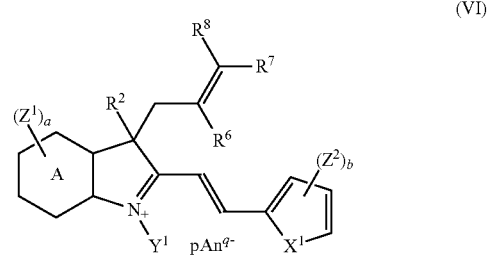

(VI)

wherein ring A, $R^2$, $Z^1$, $Z^2$, $Y^1$, a, b, $An^{q-}$, p, and q are as defined for general formula (I); $X^1$ is as defined for general formula (IV); $R^6$, $R^7$, and $R^8$ each independently represent a halogen atom, a hydroxyl group, a nitro group, a cyano group, an optionally halogen-substituted alkyl group having 1 to 4 carbon atoms, or an optionally halogen-substituted alkoxy group having 1 to 4 carbon atoms; and d represents an integer of 0 to 5.

The object of the invention is also accomplished by providing an optical recording material containing at least one indolium compound of the invention, which is used to form an optical recording layer on a substrate to provide an optical recording medium.

The object of the invention is also accomplished by providing an optical recording medium including a substrate and an optical recording layer on the substrate, the optical recording layer being formed of the optical recording material of the invention.

BEST MODE FOR CARRYING OUT THE INVENTION

The indolium compound of the invention and the optical recording material containing the indolium compound will be described in detail with their preferred embodiments.

Indolium compounds represented by general formulae (I), (IV), (V), and (VI) will be described first.

In general formulae (I), (IV), (V), and (VI), the alkyl group having 1 to 8 carbon atoms that is optionally substituted with a halogen group and optionally interrupted by —O—, —CO—, —COO—, or —COO—, which is represented by the substituent $Z^1$ of the benzene or naphthalene ring as represented by ring A and the substituent $Z^2$ of the 5- or 6-membered heterocyclic ring, may have the halogen group at any position thereof and may be interrupted by —O—, —CO—, —COO—, or —COO— at any position thereof. That is, the —O—, —CO—, —COO—, or —COO— may be bonded directly to ring A. Examples of the alkyl group having 1 to 8 carbon atoms include methyl, ethyl, propyl, isopropyl, butyl, s-butyl, t-butyl, isobutyl, amyl, isoamyl, t-amyl, hexyl, cyclohexyl, heptyl, isoheptyl, t-heptyl, n-octyl, isooctyl, t-octyl, 2-ethylhexyl, chloromethyl, dichloromethyl, trichloromethyl, trifluoromethyl, pentafluoroethyl, methoxy, ethoxy, propoxy, isopropoxy, butoxy, s-butoxy, t-butoxy, isobutoxy, amyloxy, isoamyloxy, t-amyloxy, hexyloxy, cyclohexyloxy, heptyloxy, isoheptyloxy, t-heptyloxy, n-octyloxy, isooctyloxy, t-octyloxy, 2-ethylhexyloxy, chloromethoxy, dichloromethoxy, trichloromethoxy, trifluoromethoxy, pentafluoroethoxy, 2-hydroxyethoxy, 2-methyl-2-hydroxyethoxy, 1-methyl-2-hydroxyethoxy, 3-hydroxypropoxy, 2-(2-hydroxyethoxy)ethoxy, 2-methoxyethoxy, 2-butoxyethoxy, 2-methyl-2-methoxyethoxy, 1-methyl-2-methoxyethoxy, 3-methoxypropoxy, 2-(2-methoxyethoxy)ethoxy, acetyl, acetonyl, butan-2-on-1-yl, butan-3-on-1-yl, cyclohexan-4-on-1-yl, trichloroacetyl, trifluoroacetyl, acetoxy, ethanecarbonyloxy, propanecarbonyloxy, butanecarbonyloxy, and trifluoroacetoxy. Examples of the hydrocarbon group having 1 to 8 carbon atoms possessed by the sulfonyl or the sulfinyl group represented by $Z^1$ or $Z^2$ include an alkyl group, such as methyl, ethyl, propyl, isopropyl, butyl, s-butyl, t-butyl, isobutyl, amyl, isoamyl, t-amyl, hexyl, cyclohexyl, cyclohexylmethyl, 2-cyclohexylethyl, heptyl, isoheptyl, t-heptyl, n-octyl, isooctyl, t-octyl, or 2-ethylhexyl; an alkenyl group, such as vinyl, 1-methylethen-1-yl, propen-1-yl, propen-2-yl, propen-3-yl, buten-1-yl, buten-2-yl, 2-methylpropen-3-yl, 1,1-dimethylethen-2-yl, or 1,1-dimethylpropen-3-yl; an aryl group, such as phenyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-t-butylphenyl, 2,3-dimethylphenyl, 2,4-dimethylphenyl, 2,5-dimethylphenyl, 2,6-dimethylphenyl, 3,4-dimethylphenyl, or 3,5-dimethylphenyl; and an aralkyl group, such as benzyl, 2-methylbenzyl, 3-methylbenzyl, 4-methylbenzyl, phenethyl, 2-phenylpropan-2-yl, or styryl. Examples of the alkyl group having 1 to 8 carbon atoms possessed by the alkylamino or the dialkylamide group represented by $Z^1$ or $Z^2$ include the alkyl groups recited above. Examples of the halogen group represented by $Z^1$ or $Z^2$ include fluoro, chloro, bromo, and iodo.

Examples of the ring structure formed by joining a plurality of $Z^2$ substituents in general formulae (I), (IV), (V), and (VI) include 5- to 7-membered rings, such as cyclopentane, cyclohexane, cyclopentane, benzene, piperidine, morpholine, lactone, and lactam; and fused rings, such as naphthalene and anthracene.

The organic groups having 1 to 30 carbon atoms represented by $R^2$ in general formulae (I), (IV), (V), and (VI), except those of general formulae (II), (II'), and (III), are not limited and include an alkyl group, such as methyl, ethyl, propyl, isopropyl, butyl, s-butyl, t-butyl, isobutyl, amyl, isoamyl, t-amyl, hexyl, cyclohexyl, cyclohexylmethyl, 2-cyclohexylethyl, heptyl, isoheptyl, t-heptyl, n-octyl, isooctyl, t-octyl, 2-ethylhexyl, nonyl, isononyl, decyl, dodecyl, tridecyl, tetradecyl, pentadecyl, hexadecyl, heptadecyl, or octadecyl; an alkenyl group, such as vinyl, 1-methylethenyl, 2-methylethenyl, propenyl, butenyl, isobutenyl, pentenyl, hexenyl, heptenyl, octenyl, decenyl, pentadecenyl, or 1-phenylpropen-3-yl; an alkylaryl group, such as phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-t-butylphenyl, 4-hexylphenyl, 4-cyclohexylphenyl, 4-octylphenyl, 4-(2-ethylhexyl)phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-t-butylphenyl, or cyclohexylphenyl; an arylalkyl group, such as benzyl, phenethyl, 2-phenylpropan-2-yl, diphenylmethyl, triphenylmethyl, styryl, or cinnamyl; and the hydrocarbon groups recited above which are interrupted with an ether linkage or a thioether linkage, such as 2-methoxyethyl, 3-methoxypropyl, 4-methoxybutyl, 2-butoxyethyl, methoxyethoxyethyl, methoxyethoxyethoxyethyl, 3-methoxybutyl, 2-phenoxyethyl, 2-methylthioethyl, and 2-phenylthioethyl. The above recited groups may be substituted with the following substituents.

The substituents include alkyl groups, such as methyl, ethyl, propyl, isopropyl, cyclopropyl, butyl, s-butyl, t-butyl, isobutyl, amyl, isoamyl, t-amyl, cyclopentyl, hexyl, 2-hexyl, 3-hexyl, cyclohexyl, bicyclohexyl, 1-methylcyclohexyl, heptyl, 2-heptyl, 3-heptyl, isoheptyl, t-heptyl, n-octyl, isooctyl, t-octyl, 2-ethylhexyl, nonyl, isononyl, and decyl; alkoxy groups, such as methoxy, ethoxy, propoxy, isopropoxy, butoxy, s-butoxy, t-butoxy, isobutoxy, amyloxy, isoamyloxy, t-amyloxy, hexyloxy, cyclohexyloxy, heptyloxy, isoheptyloxy, t-heptyloxy, n-octyloxy, isooctyloxy, t-octyloxy, 2-ethylhexyloxy, nonyloxy, and decyloxy; alkylthio groups, such as methylthio, ethylthio, propylthio, isopropylthio, butylthio, s-butylthio, t-butylthio, isobutylthio, amylthio, isoamylthio, t-amylthio, hexylthio, cyclohexylthio, heptylthio, isoheptylthio, t-heptylthio, n-octylthio, isooctylthio, t-octylthio, and 2-ethylhexylthio; alkenyl groups, such as vinyl, 1-methylethenyl, 2-methylethenyl, 2-propenyl, 1-methyl-3-propenyl, 3-butenyl, 1-methyl-3-butenyl, isobutenyl, 3-pentenyl, 4-hexenyl, cyclohexenyl, bicyclohexenyl, heptenyl, octenyl, decenyl, pentadecenyl, eicosenyl, and tricosenyl; arylalkyl groups, such as benzyl, phenethyl, diphenylmethyl, triphenylmethyl, styryl, and cinnamyl; aryl groups, such as phenyl and naphthyl; aryloxy groups, such as phenoxy and naphthoxy; arylthio groups, such as phenylthio and naphthylthio; heterocyclic groups, such as pyridyl, pyrimidyl, pyridazyl, piperidyl, pyranyl, pyrazolyl, triazyl, pyrrolyl, quinolyl, isoquinolyl, imidazolyl, benzimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, 2-pyrrolidinon-1-yl, 2-piperidon-1-yl, 2,4-dioxyimidazolidin-3-yl, and 2,4-dioxyoxazolidin-3-yl; halogen atoms, such as fluorine, chlorine, bromine, and iodine; acyl groups, such as acetyl, 2-chloroacetyl, propionyl, octanoyl, acryloyl, methacryloyl, phenylcarbonyl (benzoyl), phthaloyl, 4-trifluoromethylbenzoyl, pivaloyl, salicyloyl, oxaloyl, stearoyl, methoxycarbonyl, ethoxycarbonyl, t-butoxycarbonyl, n-octadecyloxycarbonyl, and carbamoyl; acyloxy groups, such as acetyloxy and benzoyloxy; an amino group; substituted amino groups, such as ethylamino, dimethylamino, diethylamine, butylamino, cyclopentylamino, 2-ethylhexylamino, dodecylamino, anilino, chlorophenylamino, toluidino, anisidino, N-methylanilino, diphenylamino, naphthylamino, 2-pyridylamino, methoxycarbonylamino, phenoxycarbonylamino, acetylamino, benzoylamino, formylamino, pivaloylamino, lauroylamino, carbamoylamino, N,N-dimethylaminocarbonylamino, N,N-diethylaminocarbonylamino, morpholinocarbonylamino, methoxycarbonylamino, ethoxycarbonylamino, t-butoxycarbonylamino, n-octadecyloxycarbonylamino, N-methyl-methoxycarbonylamino, phenoxycarbonylamino, sulfamoylamino, N,N-dimethylaminosulfonylamino, methylsulfonylamino, butylsulfonylamino, and phenylsulfonylamino; a sulfonamide group, a sulfonyl group, a carboxyl group, a cyano group, a sulfo group, a hydroxyl group, a nitro group, a mercapto group, an imide group, a carbamoyl group, and a sulfonamido group. These substituents may further be substituted. The carboxyl group and the sulfo group may form a salt.

Preferred examples of the groups represented by $R^2$ except those represented by formulae (II), (II'), and (III) are methyl, ethyl, propyl, isopropyl, butyl, s-butyl, and t-butyl.

Examples of the 5-membered heterocyclic ring represented by ring B in general formula (I) include pyrrole, furan, thiophene, pyrazolidine, pyrazole, imidazole, imidazolidine, oxazole, isoxazole, isoxazolidine, thiazole, and isothiazolidine. Examples of the 6-membered heterocyclic ring represented by ring B include piperazine, morpholine, thiomorpholine, julolidine, pyridine, pyrazine, pyrimidine, pyridazine, and triazine. The 5- or 6-membered heterocyclic ring as represented by ring B may be fused to other ring(s) or may be substituted. Examples of such rings include quinoline, isoquinoline, indole, julolidine, benzothiophene, benzoxazole, benzotriazole, azulene, and phthalimide.

Examples of the alkyl group having 1 to 10 carbon atoms represented by $Y^1$ in general formulae (I) and (IV) to (V) include methyl, ethyl, propyl, isopropyl, butyl, s-butyl, t-butyl, isobutyl, amyl, isoamyl, t-amyl, hexyl, cyclohexyl, cyclohexylmethyl, cyclohexylethyl, heptyl, isoheptyl, t-heptyl, n-octyl, isooctyl, t-octyl, 2-ethylhexyl, nonyl, isononyl, and decyl. Examples of the aryl group having 6 to 20 carbon atoms represented by $Y^1$ are phenyl, naphthyl and anthracen-1-yl, and phenanthrene-1-yl. Examples of the arylalkyl group having 7 to 20 carbon atoms represented by $Y^1$ are benzyl, phenethyl, 2-phenylpropane, diphenylmethyl, triphenylmethyl, styryl, and cinnamyl.

In general formulae (I) and (IV) to (V), examples of the anion as represented by $An^{q-}$ which is monovalent include halide anions, such as chloride ion, bromide ion, iodide ion, and fluoride ion; inorganic anions, such as perchlorate ion, chlorate ion, thiocyanate ion, hexafluorophosphate ion, hexafluoroantimonate ion, and tetrafluoroborate anion; organic sulfonate anions, such as benzenesulfonate ion, toluenesulfonate ion, trifluoromethanesulfonate ion, diphenylamine-4-sulfonate ion, 2-amino-4-methyl-5-chlorobenzenesulfonate anion, 2-amino-5-nitrobenzenesulfonate anion, and the sulfonate anion described in JP 2004-53799A; organic phosphate anions, such as octylphosphate anion, dodecylphosphate anion, octadecylphosphate anion, phenylphosphate anion, nonylphosphate anion, 2,2'-methylenebis(4,6-di-tert-butylphenyl)phosphate anion; bis(trifluoromethylsulfonyl)imide anion, bis(perfluorobutanesulfonyl)imide anion, perfluoro-4-ethylcyclohexanesulfonate anion, and tetrakis(pentafluorophenyl)borate anion. Examples of the anion $An^{q-}$ which is divalent include benzenedisulfonate anion and naphthalenedisulfonate anion. If desired, a quencher anion capable of deexciting (quenching) an active molecule in an excited state, a metallocene compound anion of, for example, a ferrocene or a ruthenocene compound having an anionic group (e.g., a carboxyl group, a phosphonic acid group, or a sulfonic acid group) on its cyclopentadienyl ring can be used.

Examples of the quencher anion include anions represented by general formulae (A) and (B) and formulae (C) and (D) shown below and those described in JP 60-234892A, JP 5-43814A, JP 5-305770A, JP 6-239028A, JP 9-309886A, JP 9-323478A, JP 10-45767A, JP 11-208118A, JP 2000-168237A, JP 2002-201373A, JP 2002-206061A, JP 2005-297407A, JP 7-96334B, and WO98/29257.

[Formula 7]

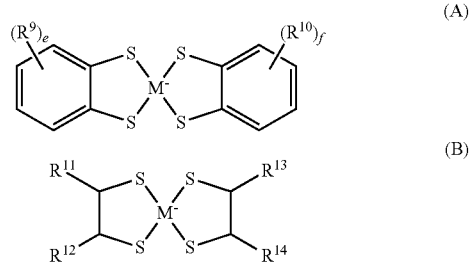

wherein M is as defined for general formula (III); $R^9$ and $R^{10}$ each independently represent a halogen atom, an alkyl group having 1 to 8 carbon atoms, an aryl group having 6 to 30 carbon atoms, or —$SO_2$-J; J represents an alkyl group, an optionally halogen-substituted aryl group, a dialkylamino group, a diarylamino group, a piperidino group, or a morpholino group; e and f each independently represent an integer of 0 to 4; and $R^{11}$, $R^{12}$, $R^{13}$, and $R^{14}$ each independently represent an alkyl group, an alkylphenyl group, an alkoxyphenyl group, or a halogenated phenyl group.

[Formula 8]

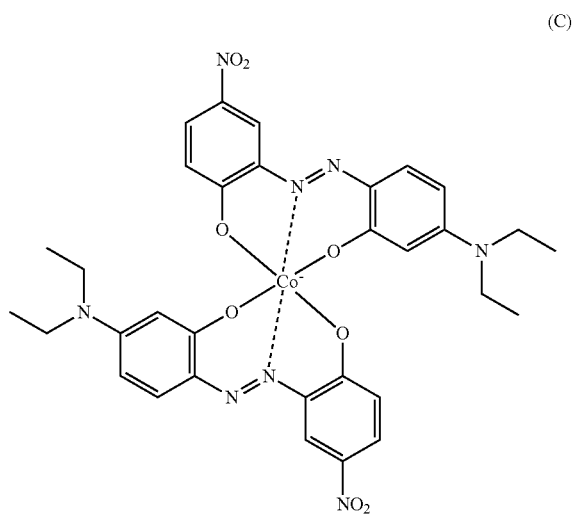

[Formula 9]

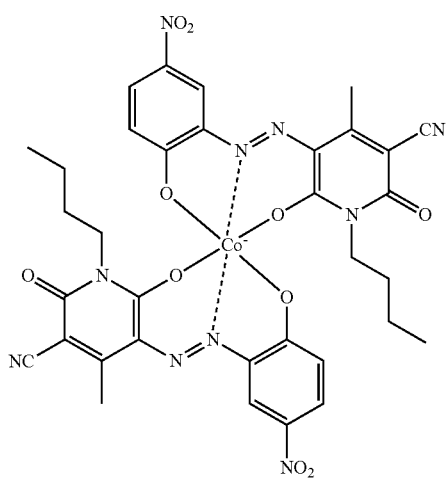

(D)

In general formula (II), examples of the optionally halogen-substituted alkyl group having 1 to 4 carbon atoms as represented by $R^{01}$, $R^{02}$, $R^{03}$, and $R^{04}$ include methyl, ethyl, propyl, isopropyl, butyl, s-butyl, t-butyl, and isobutyl. Examples of the optionally halogen-substituted alkoxy group having 1 to 4 carbon atoms include methoxy, ethoxy, propoxy, and isopropoxy. Examples of the halogen atom are fluorine, chlorine, bromine, and iodine. Examples of the cycloalkene ring formed by joining $R^{01}$ and $R^{04}$ include cyclobutene ring, cyclopentene ring, cyclohexene ring, and cyclohexadiene ring. Examples of the heterocyclic ring formed by joining $R^{01}$ and $R^{04}$ include dihydropyran ring, pyrroline ring, pyrazoline ring, indoline ring, pyrrole ring, thiophene ring, pyridine ring, pyrazine ring, pyrimidine ring, pyridazine ring, triazine ring, quinoline ring, isoquinoline ring, imidazole ring, oxazole ring, imidazolidine ring, pyrazolidine ring, isoxazolidine ring, and isothiazolidine ring. These rings may be fused with other ring(s) or may be substituted.

In general formula (II'), the 5-membered ring optionally containing a hetero atom is exemplified by cyclopentene ring, cyclopentadiene ring, imidazole ring, thiazole ring, pyrazole ring, oxazole ring, isoxazole ring, thiophene ring, furan ring, and pyrrole ring, and the 6-membered ring optionally containing a hetero atom is exemplified by benzene ring, pyridine ring, piperazine ring, piperidine ring, morpholine ring, pyrazine ring, pyrone ring, and pyrrolidine ring.

In general formula (III), examples of the alkyl group having 1 to 4 carbon atoms as represented by $R^a$, $R^b$, $R^c$, $R^d$, $R^e$, $R^f$, $R^g$, $R^h$, and $R^i$ includes methyl, ethyl, propyl, isopropyl, butyl, s-butyl, t-butyl, and isobutyl. Examples of the alkyl group a methylene moiety of which is substituted with —O— include methoxy, ethoxy, propoxy, isopropoxy, methoxymethyl, ethoxymethyl, and 2-methoxyethyl. Examples of the alkyl group a methylene moiety of which is substituted with —CO— include acetyl, 1-carbonylethyl, acetylmethyl, 1-carbonylpropyl, 2-oxobutyl, 2-acetylethyl, and 1-carbonylisopropyl.

Examples of the alkylene group having 1 to 8 carbon atoms as represented by Q in general formula (III) include methylene, ethylene, propylene, methylethylene, butylene, 1-methylpropylene, 2-methylpropylene, 1,2-dimethylpropylene, 1,3-dimethylpropylene, 1-methylbutylene, 2-methylbutylene, 3-methylbutylene, 4-methylbutylene, 2,4-dimethylbutylene, 1,3-dimethylbutylene, pentylene, hexylene, heptylene, octylene, ethane-1,1-diyl, and propane-2,2-diyl. Examples of the alkylene group whose methylene moiety is substituted with —O—, —S—, —CO—, —COO—, —COO—, —SO$_2$—, —NH—, —CONH—, —NHCO—, —N=CH—, or —CH=CH— include methyleneoxy, ethyleneoxy, oxymethylene, thiomethylene, carbonylmethylene, carbonyloxymethylene, methylenecarbonyloxy, sulfonylmethylene, aminomethylene, acetylamino, ethylenecarboxyamide, ethaneimidoyl, ethenylene, and propenylene.

The metal atom as represented by M include Fe, Co, Ni, Ti, Cu, Zn, Zr, Cr, Mo, Os, Mn, Ru, Sn, Pd, Rh, Pt, and Ir.

The alkyl group having 1 to 10 carbon atoms, the aryl group having 6 to 20 carbon atoms, or the arylalkyl group having 7 to 20 carbon atoms, optionally substituted with a halogen group and optionally interrupted by —O—, —CO—, —COO—, or —COO— as represented by $R^5$ in general formulae (IV) to (VI) may have a halogen group at any position and may be interrupted by —O—, —CO—, —OCO—, or —COO— at any position. Examples of the alkyl group having 1 to 10 carbon atoms, the aryl group having 6 to 20 carbon atoms, and the arylalkyl group having 7 to 20 carbon atoms, include the same examples respectively described with respect to $Y^1$.

Examples of the halogen atom as represented by $Z^4$ in general formula (V) and $R^6$, $R^7$, or $R^8$ in general formula (VI) include fluorine, chlorine, iodine, and iodine. Examples of the optionally halogen-substituted alkyl group having 1 to 4 carbon atoms include methyl, ethyl, propyl, isopropyl, butyl, s-butyl, t-butyl, isobutyl, and 2-chloroethyl. Examples of the optionally halogen-substituted alkoxy group having 1 to 4 carbon atoms include methoxy, ethoxy, propoxy, isopropoxy, and 2-chloroethoxy.

Of the indolium compounds according to the invention preferred are those represented by general formula (IV) in terms of low production cost and large molar absorptivity. The compounds represented by general formulae (V) and (VI) are more preferred in terms of production convenience and their optical absorption characteristics suitable for use as an optical recording material.

Preferred examples of the compounds of general formula (I) include compound Nos. 1 through 41, whose structural formulae are illustrated below in which only cations are shown. The polymethine chain in the compounds of the invention may take on a resonant structure.

[Formula 10]

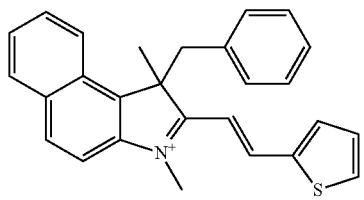

Compound No.1

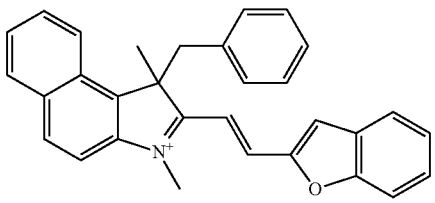

Compound No.2

-continued
Compound No.3
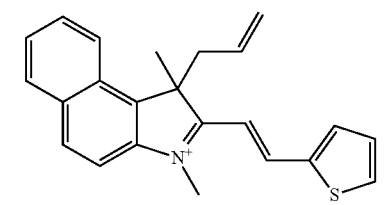
Compound No.4
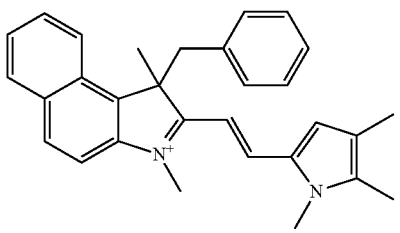
Compound No.5
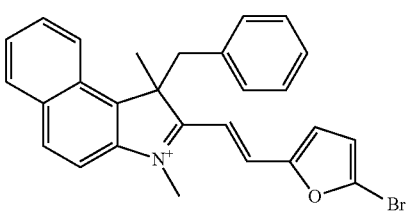
Compound No.6
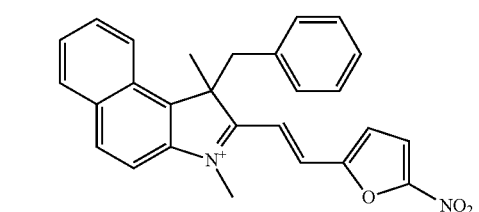
Compound No.7
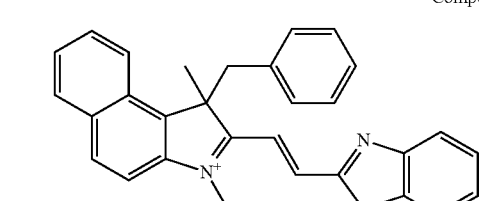
Compound No.8
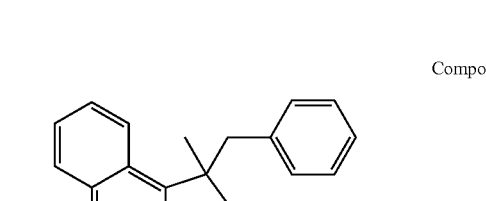
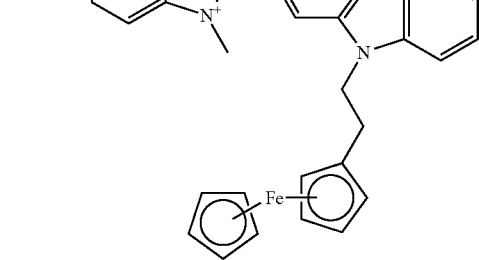
-continued
Compound No.9
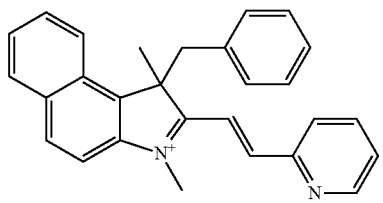
Compound No.10
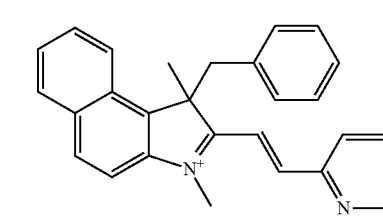
Compound No.11
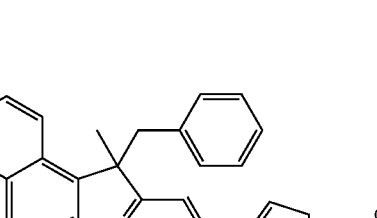
Compound No.12
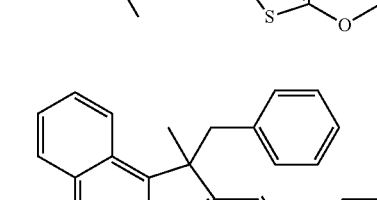
Compound No.13
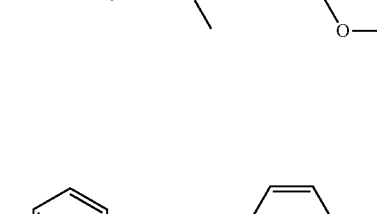
Compound No.14
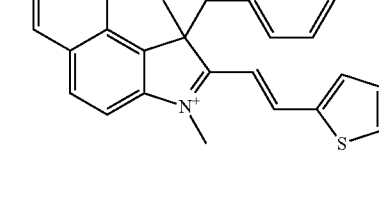
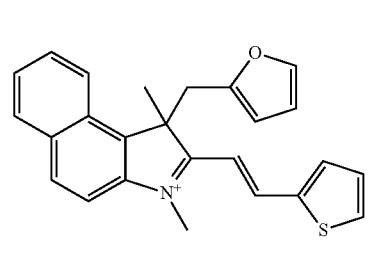

[Formula 11]
Compound No.15
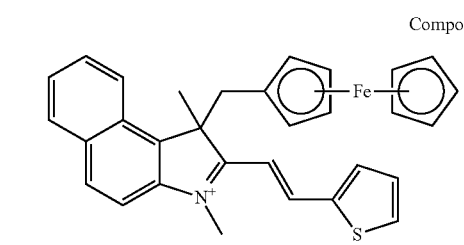
Compound No.16
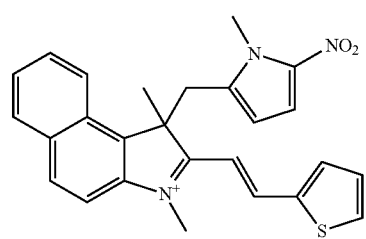
Compound No.17
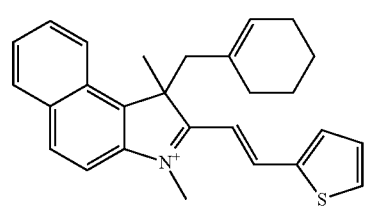
Compound No.18
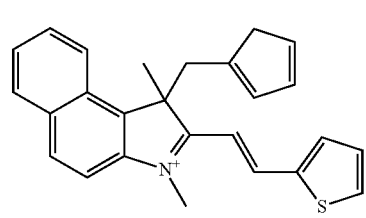
Compound No.19
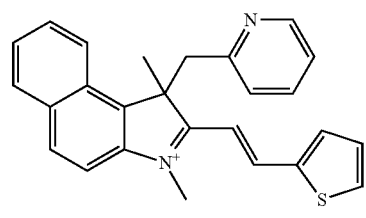
Compound No.20
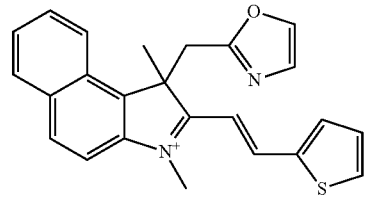
Compound No.21
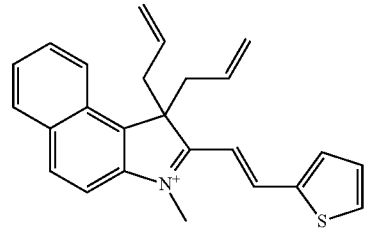
Compound No.22
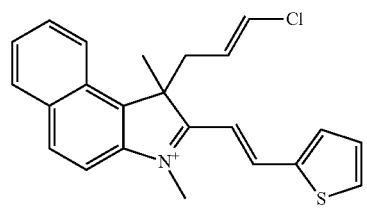
Compound No.23
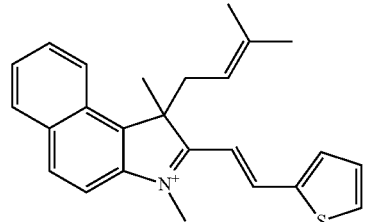
Compound No.24
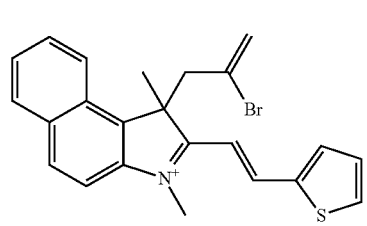
Compound No.25
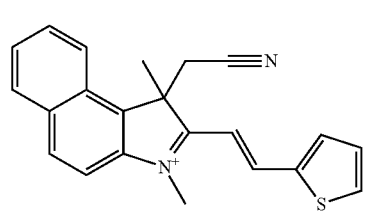
Compound No.26
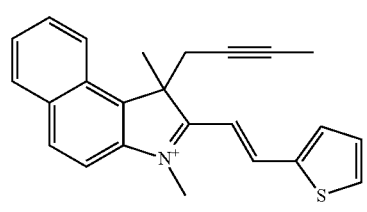
Compound No.27
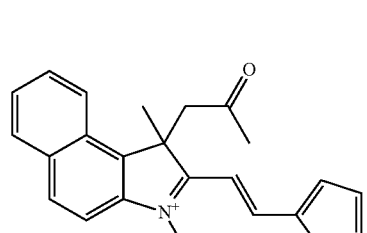
Compound No.28
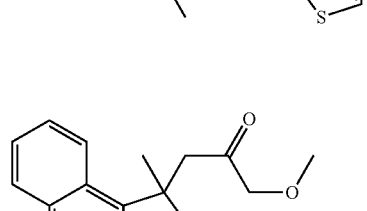

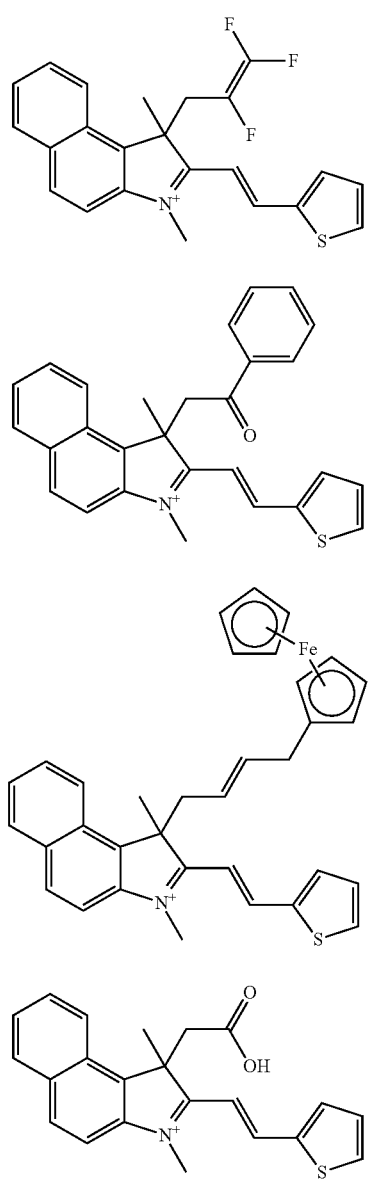
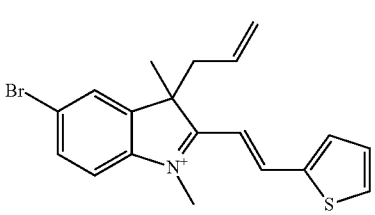
Some of the indolium compounds represented by general formula (I) of the invention embrace optical isomers including enantiomers, diastereomers, and racemates thereof having a chiral center at the asymmetric atom to which $R^1$ and $R^2$ are bonded. Any of these optical isomers, either individual or mixed, is usable.

The indolium compounds of general formula (I) are not restricted by the process of preparation. The indolium compound of general formula (I) may be synthesized by, for example, the condensation between a 2-methylindole derivative and an aromatic aldehyde derivative, followed by salt exchange.

The group having a multiple bond represented by general formula (II) or (II') can be introduced in the course of preparing a 2-methylindole derivative as an intermediate. For example, an arylhydrazine derivative as a starting material is allowed to react with a 2-butanone derivative having the multiple bond group of general formula (II) or (II') to form an indole ring, or a halogenated derivative is allowed to react on an indole ring. Y can be introduced by using Y-D (wherein D is a halogen group, e.g., chlorine, bromine or iodine, or a sulfonyloxy group, e.g., phenylsulfonyloxy, 4-methylphenylsulfonyloxy or 4-chlorophenylsulfonyloxy) reactive with NH of an indole ring. The 2-butanone derivative having the multiple bond group represented by general formula (II) or (II') can be obtained by the reaction between acetone and an aldehyde having the multiple bond group.

The indolium compound of the invention is useful not only as an optical recording material but also as an optical element, such as a light absorber used in an optical filter, an intermediate for synthesis of pharmaceuticals, agricultural chemicals, perfumes, dyes, and so forth, or a raw material of various polymers useful as functional materials. Nevertheless, the invention is not limited by these applications.

The optical recording material and the optical recording medium according to the invention will then be described.

The optical recording material of the invention contains at least one of the above described indolium compounds. The optical recording medium of the invention is obtained by forming an optical recording layer of the optical recording material on a substrate.

The method of preparing the optical recording material of the invention and the method of making the optical recording medium of the invention having an optical recording layer of the optical recording material provided on a substrate are not particularly limited. A wet coating technique is generally used to make the optical recording medium, in which an optical recording material in the form of solution is applied to a substrate by spin coating, spraying, dipping or a like method. The optical recording material in the form of solution is prepared by dissolving the indolium compound of the invention and, if necessary, various compounds described later in an organic solvent. Examples of the organic solvent include lower alcohols, such as methanol and ethanol; ether alcohols, such as methyl cellosolve, ethyl cellosolve, butyl cellosolve, and butyl diglycol; ketones, such as acetone, methyl ethyl ketone, methyl isobutyl ketone, cyclohexanone, and diacetone alcohol; esters, such as ethyl acetate, butyl acetate, and methoxyethyl acetate; acrylic esters, such as ethyl acrylate and butyl acrylate; fluoroalcohols, such as 2,2,3,3-tetrafluoropropanol; hydrocarbons, such as benzene, toluene, and xylene; and chlorinated hydrocarbons, such as methylene dichloride, dichloroethane, and chloroform. The formation of the optical recording layer may also be achieved by vapor deposition, sputtering, or a like technique. In the case of using an organic solvent, the amount of the organic solvent is preferably such that the concentration of the indolium compound in the optical recording material of the invention may range from 0.1% to 10% by mass.

The optical recording layer is formed as a thin film with a thickness usually of from 0.001 to 10 µm, preferably 0.01 to 5 µm.

The content of the indolium compound in the optical recording material of the invention is preferably 10% to 100% by mass based on the solids content. The optical recording layer is preferably formed such that the content of the indolium compound in the optical recording layer ranges from 50% to 100% by mass. Accordingly, it is more preferred for the optical recording material of the invention to contain 50% to 100% by mass of the indolium compound based on the solids content to give the above-recited preferred indolium compound content in the optical recording layer.

The term "solids content of the optical recording material of the invention" refers to the total amount of components other than non-solid components including an organic solvent. The solids content of the optical recording material is preferably 0.01% to 100% by mass, more preferably 0.1% to 10% by mass.

Where necessary, the optical recording material of the invention may contain, in addition to the indolium compound, compounds commonly employed in an optical recording layer, such as azo compounds, phthalocyanine compounds, oxonol compounds, squarylium compounds, indole compounds, styryl compounds, porphin compounds, azulenium compounds, croconic methine compounds, pyrylium compounds, thiopyrylium compounds, triarylmethane compounds, diphenylmethane compounds, tetrahydrocholine compounds, indophenol compounds, anthraquinone compounds, naphthoquinone compounds, xanthene compounds, thiazine compounds, acridine compounds, oxazine compounds, spiropyran compounds, fluorene compounds, and rhodamine compounds. The optical recording material may further contain resins, such as polyethylene, polyester, polystyrene, and polycarbonate; surfactants, antistatic agents, lubricants, flame retardants, radical scavengers (e.g., hindered amines), pit formation accelerators (e.g., ferrocene derivatives), dispersants, antioxidants, crosslinking agents, light resistance imparting agents, and so on. The optical recording material may furthermore contain an aromatic nitroso compound, an aminium compound, an iminium compound, a bisiminium compound, a transition metal chelate compound, and the like as a quencher, e.g., for singlet oxygen. The content of these various compounds in the optical recording material is up to 50% by mass based on the solids content of the optical recording material.

The optical recording material of the invention may contain a diimmonium compound. Incorporation of a diimmonium compound is effective in preventing the resulting optical recording medium from reducing the absorbance retention with time. The amount of the diimmonium compound, if added, is preferably up to 99%, more preferably 50% to 95%, by mass based on the solids content of the optical recording material of the invention.

The substrate on which the optical recording layer is provided may be of any material as long as it is substantially transparent to a write/read (recording/reproducing) light beam, including resins, such as polymethyl methacrylate, polyethylene terephthalate, and polycarbonate, and glass. The substrate may have any shape according to use, including a tape, a drum, a belt, and a disk.

A reflective layer of gold, silver, aluminum, copper, etc. may be formed on the optical recording layer by vacuum evaporation or sputtering. A protective layer may be formed using, for example, an acrylic resin or a UV curing resin.

The optical recording material of the invention is suitable to form an optical recording layer of optical recording media that employ a semiconductor laser for writing and reading, especially, known high-speed single-layer, dual-layer, or multi-layer optical discs, such as CD-Rs, DVD±Rs, HD-DVD-Rs, and BD-Rs.

EXAMPLES

The present invention will now be illustrated in greater detail with reference to Examples, Comparative Example, and Evaluation Examples, but it should be understood that the invention is not construed as being limited thereto.

Preparation Examples 1 through 4 describe preparation of compound Nos. 1 to 3 of general formula (I) in the form of perchlorate and compound No. 1 in the form of quencher (C) salt. Examples 1 through 4 illustrate production of optical recording materials and optical recording media Nos. 1 to 4 using the compound Nos. 1 to 3 obtained in Preparation Examples 1 to 4.

Comparative Example 1 shows the production of a comparative optical recording material and a comparative optical recording medium No. 1 using an indolium compound having a different structure from that of the indolium compound of general formula (I).

In Evaluation Example 1 and Comparative Evaluation Example 1, the optical recording medium No. 1 obtained in Example 1 and the comparative optical recording medium No. 1 obtained in Comparative Example 1 were evaluated for heat resistance by determining the absorbance retention at the absorption maximum wavelength ($\lambda_{max}$) of the UV absorption spectrum. The results obtained are shown in Table 5 below.

Preparation Examples 1 to 4

Preparation of Compound Nos. 1 to 3 in Perchlorate Form and Compound No. 1 in Quencher (C) Salt Form Compound Nos. 1 to 3 were synthesized in accordance with the methods described below. The resulting compounds were identified by IR and $^1$H-NMR analyses. Table 1 shows the yields and characteristics (absorption characteristics as a solution ($\lambda_{max}$ and $\epsilon$ at $\lambda_{max}$) and decomposition temperature) of the resulting compounds. Tables 2 and 3 furnish the identification data. The decomposition temperature (decomp. temp.) shown in Table 1 is a mass loss onset temperature in differential thermal analysis at a rate of temperature rise of 10° C./min.

Preparation Examples 1 to 3

Preparation of Compound Nos. 1 to 3 in ClO$_4$ Salt Form

A reactor was charged with 24 mmol of indolenine quaternary salt (bromide), 30 mmol of thiophene-2-carboxyaldehyde or benzofuran-2-carboxyaldehyde, and 38 g of chloroform, and the mixture was stirred at 80° C. for 7 hours. To the reaction mixture were added 30 mmol of sodium perchlorate and 30 g of water, followed by stirring at 60° C. for 1 hour, followed by oil/water separation. The solvent was removed by evaporation. The residue was recrystallized from 20 ml of chloroform to give compound No. 1, 2 or 3 in ClO$_4$ salt form.

Preparation Example 4

Preparation of Compound No. 1 in Quencher (C) Salt Form

A reactor was charged with 0.69 mmol of compound No. 1 in ClO$_4$ salt form, 0.69 mmol of a triethylamine salt of an anion represented by chemical formula (C) described supra, and 3.6 g of pyridine, and the mixture was stirred at 60° C. for 2 hours. After addition of 8 g of methanol, the reaction mixture was cooled to room temperature. The solid precipitated was collected by filtration and dried under reduced pressure to yield compound No. 1 in quencher anion (C) salt form.

TABLE 1

| Prepn. Example No. | Indolium Compound Cation | Indolium Compound Anion | Yield (%) | $\lambda_{max}$ (%) | $\epsilon$ (×10$^4$) | Decomp. Temp. (° C.) |
|---|---|---|---|---|---|---|
| 1 | compound No. 1 | ClO$_4^-$ | 26 | 442.5 | 1.64 | 204 |
| 2 | compound No. 2 | ClO$_4^-$ | 26 | 419.0 | 1.65 | 205 |
| 3 | compound No. 3 | ClO$_4^-$ | 24 | 441.5 | 1.98 | 196 |
| 4 | compound No. 1 | quencher (C) | 56 | 542.0 | 7.12 | 215 |

TABLE 2

| Prepn. Example No. | Indolium Compound Cation | Indolium Compound Anion | IR Absorption Spectrum (cm$^{-1}$) |
|---|---|---|---|
| 1 | compound No. 1 | ClO$_4^-$ | 3435, 3086, 1597, 1577, 1540, 1496, 1452, 1398, 1356, 1316, 1277, 1247, 1227 |
| 2 | compound No. 2 | ClO$_4^-$ | 3433, 3057, 1597, 1557, 1523, 1504, 1456, 1397, 1352, 1299, 1226 |
| 3 | compound No. 3 | ClO$_4^-$ | 3433, 3088, 1597, 1577, 1543, 1523, 1499, 1458, 1397, 1355, 1311, 1277, 1244 |
| 4 | compound No. 1 | quencher (C) | 3465, 3066, 2928, 1610, 1577, 1517, 1461, 1389, 1322, 1260 |

TABLE 3

| Prepn. Example No. | Indolium Compound Cation | Indolium Compound Anion | $^1$H-NMR (DMSO-d6) |
|---|---|---|---|
| 1 | compound No. 1 | ClO$_4^-$ | 8.94 (d, 1H), 8.65 (d, 1H), 8.24-8.18 (m, 4H), 7.90-7.73 (m, 3H), 7.45-7.41 (m, 2H), 6.96 (t, 1H), 6.85 (t, 2H), 6.38 (d, 2H), 4.08 (dd, 2H), 3.99 (s, 3H), 2.15 (s, 3H) |

TABLE 3-continued

| Prepn. Example No. | Indolium Compound | | $^1$H-NMR (DMSO-d6) |
|---|---|---|---|
| | Cation | Anion | |
| 2 | compound No. 2 | $ClO_4^-$ | 8.77 (d, 1H), 8.69 (d, 1H), 8.22 (d, 2H), 7.97-7.88 (m, 4H), 7.80-7.75 (m, 2H), 7.63-7.59 (m, 2H), 7.43 (t, 1H), 6.96 (t, 1H), 6.85 (t, 2H), 6.39 (d, 2H), 4.16-4.06 (m, 5H), 2.19 (s, 3H) |
| 3 | compound No. 3 | $ClO_4^-$ | 8.82 (d, 1H), 8.48 (d, 1H), 8.27 (d, 1H), 8.21-8.18 (m, 3H), 8.07 (d, 1H), 7.80 (t, 1H), 7.71 (t, 1H), 7.41-7.37 (m, 2H), 4.88 (m, 1H), 4.72-4.60 (m, 2H), 4.23 (s, 3H), 3.61-3.43 (m, 2H), 2, 02 (s, 3H) |
| 4 | compound No. 1 | quencher (C) | 9.00 (d, 2H), 8.96 (d, 1H), 8.23-8.17 (m, 4H), 7.89-7.80 (m, 4H), 7.74 (t, 1H), 7.64 (d, 1H), 7.44-7.40 (m, 2H), 6.95 (t, 1H), 6.84 (t, 2H), 6.55 (d, 2H), 6.37-6.33 (m, 4H), 5.73 (d, 2H), 4.70 (q, 2H), 3.96 (s, 3H), 3.28 (q, 8H), 2.07 (s, 3H), 1.00 (t, 12H) |

Examples 1 to 4

Each of the compounds obtained in Preparation Examples 1 to 4 was dissolved in 2,2,3,3-tetrafluoropropanol in a concentration of 1.0% by mass to prepare a solution as an optical recording material. A titanium chelate compound T-50 (available from Nippon Soda Co., Ltd.) was applied to a 12 cm diameter polycarbonate disk substrate, followed by hydrolysis to form a primer layer having a thickness of 0.01 μm. The optical recording material was applied onto the primer layer by spin coating to form an optical recording layer having a thickness of 100 nm. The resulting optical recording media were designated as optical recording medium Nos. 1 to 4. The optical recording medium Nos. 1 to 4 were measured for UV absorption spectrum and UV reflection (incidence angle: 5°, on the optical recording layer) spectrum. The results obtained are shown in Table 4.

TABLE 4

| Example No. | Indolium Compound | | $\lambda_{max}$ | | $\lambda_{max}$ of Reflected Light(nm)/ |
|---|---|---|---|---|---|
| | Cation | Anion | (nm) | r405* | Reflectance (%) |
| 1 | compound No. 1 | $ClO_4^-$ | 465 | 0.73 | 513/24.2 |
| 2 | compound No. 2 | $ClO_4^-$ | 477 | 0.65 | 517/22.1 |
| 3 | compound No. 3 | $ClO_4^-$ | 453 | 0.83 | 495/22.9 |
| 4 | compound No. 1 | quencher (C) | 560 | 0.61 | 584/38.9 |

*r405: ratio of molar absorptivity at 405 nm to that at $\lambda_{max}$

Comparative Example 1

An optical recording material was prepared in the same manner as in Examples 1 to 4 except for using comparative compound No. 1 shown below in place of the indolium compound of the invention. An optical recording medium (designated No. 1) was made using the resulting optical recording material in the same manner as in Examples 1 to 4.

[Formula 13]

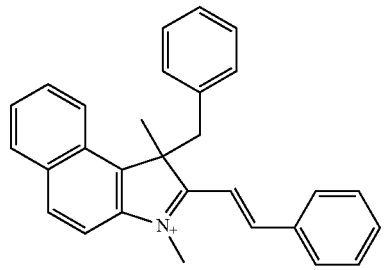

Comparative compound No.1

Evaluation Example 1 and Comparative Evaluation Example 1

Optical recording medium No. 1 obtained in Example 1 and comparative optical recording medium No. 1 obtained in Comparative Example 1 were evaluated for heat resistance. The recording medium was placed in a hot air circulating thermostat dryer set at 80° C. for 120 hours. The UV absorption spectra measured before and after the heating were compared to calculate an absorbance retention at the $\lambda_{max}$ of the UV absorption spectrum before the heating. The results obtained are shown in Table 5.

TABLE 5

| | Optical Recording Medium | Indolium Compound | | Retention after 120 hrs (%) |
|---|---|---|---|---|
| | | Cation | Anion | |
| Evaluation Example 1 | optical recording medium No. 1 | compound No. 1 | $ClO_4^-$ | 92.7 |
| Comparative Evaluation Example 1 | comparative optical recording medium No. 1 | comparative compound No. 1 | $ClO_4^-$ | 84.0 |

As is apparent from Table 5, the optical recording medium having an optical recording layer formed of the optical recording material of the invention exhibits a high absorbance retention even after being heated at 80° C. for 120 hours. The comparative optical recording medium having an optical recording layer formed of the comparative optical recording material containing the comparative compound suffers from a considerable reduction in absorbance retention, proving to have poor heat resistance.

INDUSTRIAL APPLICABILITY

The present invention provides an indolium compound suited to form an optical recording layer of an optical recording medium and an optical recording material containing the indolium compound. The indolium compound according to the invention has a low decomposition temperature and therefore exhibits low heat storage properties and is able to suppress thermal interference. The compound has high light resistance and is suited to form an optical recording layer of an optical recording medium.

What is claimed is:

1. An optical recording medium comprising a substrate and an optical recording layer on the substrate, the optical recording layer being formed of an optical recording material comprising at least one indolium compound represented by general formula (IV):

[Formula IV]

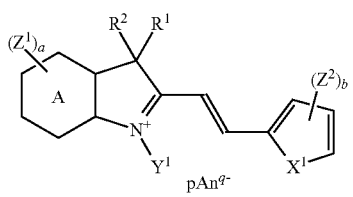

(IV)

wherein ring A represents a naphthalene ring; $R^1$ represents a group represented by general formula (II), (II'), or (III); $R^2$ represents an organic group having 1 to 30 carbon atoms or a group represented by general formula (II), (II'), or (III); $Y^1$ represents a hydrogen atom or an alkyl group having 1 to 10 carbon atoms; $Z^1$ and $Z^2$ each represent an alkyl group having 1 to 8 carbon atoms optionally substituted with a halogen group and optionally interrupted by —O—, —CO—, —OCO—, or —COO—, a sulfonyl group having a hydrocarbon group having 1 to 8 carbon atoms, a sulfinyl group having a hydrocarbon group having 1 to 8 carbon atoms, a group represented by general formula (III), a cyano group, a nitro group, a hydroxyl group, or a halogen group; a plurality of $Z^2$ substituents may be joined to form a ring structure; a represents an integer of 0 to 6; b represents an integer of 0 to 5; $pAn^{q-}$ represents $ClO_4^-$; $X^1$ represents —$NR^5$—, an oxygen atom, a sulfur atom, or a selenium atom; and $R^5$ represents a hydrogen atom, an alkyl group having 1 to 10 carbon atoms, an aryl group having 6 to 20 carbon atoms, or an arylalkyl group having 7 to 20 carbon atoms, the alkyl, the aryl, and the arylalkyl groups being optionally substituted with a halogen group and optionally interrupted by —O—, —CO—, —OCO—, or —COO—,

[Formula II and Formula II']

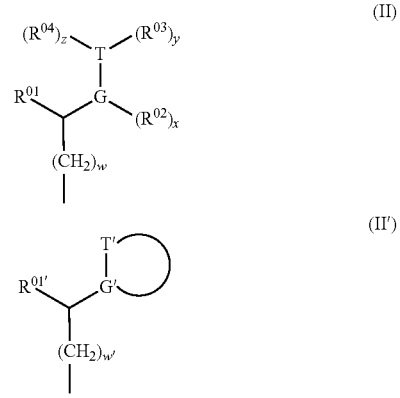

in general formula (II), the bond between G and T is a double bond, a conjugated double bond, or a triple bond; G represents a carbon atom; T represents a carbon atom, an oxygen atom, or a nitrogen atom; x, y, and z each represent 0 or 1, provided that, when T is oxygen, y=z=0, and, when T is nitrogen, y+z=0 or 1; w represents an integer of 0 to 4; $R^{01}$, $R^{02}$, $R^{03}$, and $R^{04}$ each independently represent a hydrogen atom, a hydroxyl group, a nitro group, a cyano group, a halogen atom, an alkyl group having 1 to 4 carbon atoms optionally substituted with a halogen atom, or an alkoxy group having 1 to 4 carbon atoms optionally substituted with a halogen atom; $R^{01}$ and $R^{04}$ may be joined to form a cycloalkene ring or a heterocyclic ring, in general formula (II'), the bond between G' and T' is a double bond or a conjugated double bond; G' represents a carbon atom; T' represents a carbon atom or a nitrogen atom; w' represents an integer of 0 to 4; $R^{01'}$ represents a hydrogen atom, a hydroxyl group, a nitro group, a cyano group, a halogen atom, an alkyl group having 1 to 4 carbon atoms optionally substituted with a halogen atom, or an alkoxy group having 1 to 4 carbon atoms optionally substituted with a halogen atom; the ring containing G' and T' is a 5-membered ring optionally containing a hetero atom, a 6-membered ring optionally containing a hetero atom, a naphthalene ring, a quinoline ring, an isoquinoline ring, an anthracene ring, or an anthraquinone ring; the ring containing G' and T' may be substituted with a halogen atom, a hydroxyl group, a nitro group, a cyano group, an alkyl group having 1 to 4 carbon atoms, or an alkoxy group having 1 to 4 carbon atoms,

[Formula III]

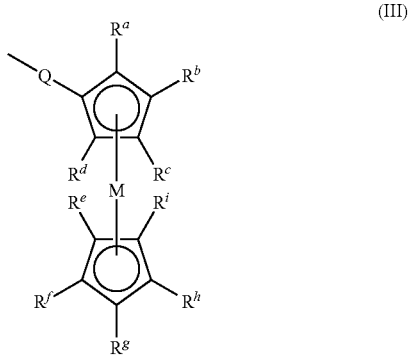

wherein $R^a$, $R^b$, $R^c$, $R^d$, $R^e$, $R^f$, $R^g$, $R^h$, and $R^i$ each independently represent a hydrogen atom or an alkyl group having 1 to 4 carbon atoms a methylene moiety of which may be displaced by —O— or —CO—; Q represents a single bond or an optionally substituted alkylene group having 1 to 8 carbon atoms a methylene moiety of which may be displaced by —O—, —S—, —CO—, —OCO—, —OCO—, —SO$_2$—, —NH—, —CONH—, —NHCO—, —N=CH—, or —CH=CH—; and M represents Fe, Co, Ni, Ti, Cu, Zn, Zr, Cr, Mo, Os, Mn, Ru, Sn, Pd, Rh, Pt, or Ir.

* * * * *